(12) United States Patent
Liang

(10) Patent No.: US 10,188,731 B2
(45) Date of Patent: Jan. 29, 2019

(54) METHODS FOR KILLING CANCER CELLS AND CELLULAR IMAGING USING MAGNETO-ELECTRIC NANO-PARTICLES AND EXTERNAL MAGNETIC FIELD

(71) Applicant: Ping Liang, Newport Coast, CA (US)

(72) Inventor: Ping Liang, Newport Coast, CA (US)

(73) Assignee: Ping Liang, Newport Coast, CA (US)

( * ) Notice: Subject to any disclaimer, the term of this patent is extended or adjusted under 35 U.S.C. 154(b) by 17 days.

(21) Appl. No.: 15/326,545

(22) PCT Filed: Aug. 13, 2015

(86) PCT No.: PCT/US2015/045148
§ 371 (c)(1),
(2) Date: Jan. 16, 2017

(87) PCT Pub. No.: WO2016/025768
PCT Pub. Date: Feb. 18, 2016

(65) Prior Publication Data
US 2017/0224822 A1    Aug. 10, 2017

Related U.S. Application Data

(60) Provisional application No. 62/037,447, filed on Aug. 14, 2014.

(51) Int. Cl.
| | | |
|---|---|---|
| *A61K 9/14* | (2006.01) | |
| *A61K 41/00* | (2006.01) | |
| *A61K 9/51* | (2006.01) | |
| *A61K 9/00* | (2006.01) | |
| *A61K 49/18* | (2006.01) | |
| *A61N 1/40* | (2006.01) | |
| *A61N 1/32* | (2006.01) | |

(52) U.S. Cl.
CPC ........ *A61K 41/0052* (2013.01); *A61K 9/0009* (2013.01); *A61K 9/0019* (2013.01); *A61K 9/5115* (2013.01); *A61K 49/1818* (2013.01); *A61N 1/327* (2013.01); *A61N 1/40* (2013.01)

(58) Field of Classification Search
CPC ........... A61F 7/00; A61F 7/12; A61K 9/0009; A61K 41/0028; A61N 1/327
See application file for complete search history.

(56) References Cited

U.S. PATENT DOCUMENTS

| | | | | |
|---|---|---|---|---|
| 2003/0032995 A1* | 2/2003 | Handy | ................... | A61N 1/406 607/103 |
| 2008/0286366 A1* | 11/2008 | Fischer | .............. | A61K 31/7088 424/489 |
| 2009/0123384 A1* | 5/2009 | Wald | .................. | G01R 33/5601 424/9.32 |

* cited by examiner

*Primary Examiner* — Micah Paul Young
(74) *Attorney, Agent, or Firm* — Guosheng Wang; United States Research and Patent Firm

(57) ABSTRACT

This invention provides methods for achieving high-specificity killing of targeted cells using Magneto-Electric Nano-Particles (MENPs). Embodiments comprise injecting into a patients body manufactured MENPs that have a higher tendency to accumulate near or attach to targeted cells through one or more physical forces and/or biological mechanisms; and applying a magnetic field to the MENPs to generate actions that are sufficient to cause death of the targeted cells.

16 Claims, 4 Drawing Sheets

10  11
Magnetic disk  Hole for injection needle
a 15  16
Electromagnet  Hole for injection needle
b 17
Current Driver and Controller

METHODS FOR KILLING CANCER CELLS AND CELLULAR IMAGING USING MAGNETO-ELECTRIC NANO-PARTICLES AND EXTERNAL MAGNETIC FIELD

FIELD OF INVENTION

This invention relates generally to using magneto-electric materials to kill cancer or diseased cells and for cellular imaging, and more specifically to controlling the behavior or properties of Magneto-Electric Nano-Particles (MENPs) that penetrate into or bound to cancer cells to kill the cancer or diseased cells, and to using magneto-electric coupling of MENPs for cellular imaging.

BACKGROUND

Like conventional magnetic nano-particles (MNPs), e.g. gadolinium- or magnetite-based, MENPs have a non-zero magnetic moment and therefore their spatial position can be remotely controlled via application of a magnetic field gradient. However, unlike MNPs, MENPs have another property, energy-efficient control of the intrinsic electric fields of MENPs by an external magnetic field. This unique capability is a result of the intrinsic magneto-electric (ME) coupling (due to the correlated magnetostrictive and piezo-electric effects) in this new class of nanostructures even at body temperature. As a result, when introduced in a biological microenvironment MENPs act as local magnetic-to-electric-field nano-converters. Consequently, MENPs are capable of distinguishing cancer cells from healthy cells by locally probing the cell membranes' electric properties, making use of the difference between the (electroporation) electrical potentials of cancer cells and healthy cells. It is known that a cancer cell's membrane porosity can be significantly increased (to allow particle and/or drug penetration through the cell membrane into cytosol) by application of a relatively high electric field (of the order of 1000 V/cm), but it takes a substantially higher field (by a factor of three or more) to achieve the same drug-penetrability effect into the healthy cells (Binggeli et al., 1980). This effect is widely known as electroporation (Cahill et al., 2010). The problem with the conventional macroscopic electroporation effect in treating cancer is the need to apply relatively high electric fields (>1000 V/cm) over a relatively large region of the body; as a result, the treatment requires relatively high energies and is accompanied with side effects because of significant energy dissipation, which in turn makes its use highly limited. Prior art in (Guduru et al 2013) effectively creates a remote-magnetic-field-controlled electroporation effect in the vicinity of the MENPs only and therefore can enable highly selective electroporation of cancer cells at a small fraction of energy with no destructive energy dissipation when an external magnetic field of a certain range of strength is applied.

Prior art (Guduru et al. 2013) used drug-coated MENPs to carry drugs inside cancer cells to kill the cancer cells. These represent a significant advance, however, drugs are still used, which can have side effects. There is no prior art that provides mechanism for cancer cell targeting and killing mechanisms using the methods or apparatus described in this application.

DETAILED DESCRIPTION

Figure 1:
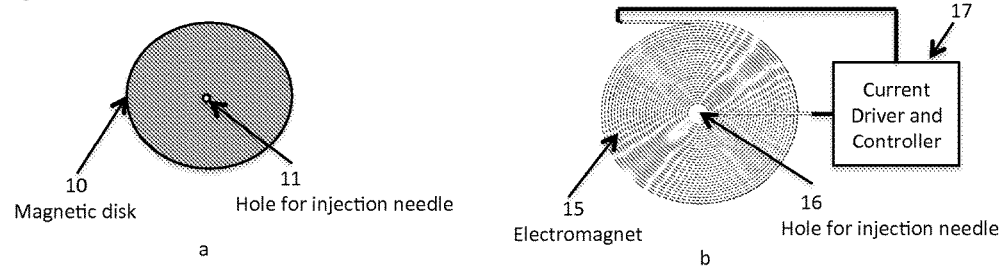
FIG. 1 shows a magnet disk and an electromagnet apparatus used to generate external magnetic field to control MENPs.

Reference may now be made to the drawings wherein like numerals refer to like parts throughout. Exemplary embodiments of the inventions may now be described. The exemplary embodiments are provided to illustrate aspects of the inventions and should not be construed as limiting the scope of the inventions. When the exemplary embodiments are described with reference to block diagrams or flowcharts, each block may represent a method step or an apparatus element for performing the method step.

The present inventions provide methods, processes or construction of an apparatus for using the unique physics of MENPs to achieve high-specificity killing of cancer cells via application of an external magnetic field to generate an electric field and/or mechanical motion after one or more MENPs have penetrated the cancer cells' membrane, without loading or coating any drug on the MENPs, and causing no harm or only minimum harm to normal cells.

In both cases (drug-loaded MENPs or MENPs alone), the MENPs have a non-zero magnetic moment and therefore, if administrated in a patient's body, can be remotely navigated through the blood circulation and/or lymph systems via application of adequately high remote magnetic field gradients (e.g., >1000 Oe/cm). The MENPs can be administrated via subcutaneous (SC) intratumoral (IT), peritumoral (PT), intraperitoneal (IP), or intravenous (IV) injection, or oral intake (OI), or by other means.

In case of IT, IP or PT injection, the passive targeting is initiated externally (by injecting directly into or near the tumor). One embodiment applies an external magnet field that serves to attract the MENPs at the tumor site and/or to cause the MENPs to penetrate the membrane of cancer cells. The magnetic field can be applied either via permanent magnets or electromagnets depending on the size and shape of the tumor. The external magnetic field is applied prior to or at the time of the IT, IP or PT injection and is maintained afterwards for a period of time. The strength of the external magnetic field is chosen to be (1) sufficiently strong to overcome the viscosity of the cellular microenvironment, preventing nano-particles from moving to other parts via circulation of body fluids and further amplifying the well-known Enhanced Permeability and Retention (EPR) effect that nano-particles tend to accumulate in tumor tissue much more than they do in normal tissue, (2) sufficiently strong to cause the MENPs to penetrate the membrane of cancer cells, but (3) not too strong to cause the MENPs to penetrate the membrane of normal cells. At a second stage, after the MENPs are inside the cancer cells, one embodiment applies an external magnetic field to generate local electric fields on the MENPs via the magnetic-electric (ME) coupling characteristics of the MENPs. When the electric field is sufficiently strong, it disrupts the mechanisms of the cancer cells or kills the cancer cell by electric shock. In another embodiment, the MENPs are coated with drugs and the combination of the electric field and drug kills the cancer cells.

One embodiment for targeting with IT, IP or PT injection uses a permanent magnetic disk 10 with a hole 11 in the middle for the needle to go through, illustrated in FIG. 1a. The disk is first applied to the targeted site prior to or at the time of injection. The shape and magnetic field strength of the disk can be customized to the targeted site, where the required magnetic field strength is achieved by selecting the material and thickness of the disk. Another embodiment for targeting with IT, IP or PT injection uses an electromagnet 15 with a hole 16 in the middle whose size and shape is matched with the targeted site, and the required the magnetic field strength is achieved by selecting the number of windings of the coils and/or the amount and or frequency of electric current applied by a Current Driver and Controller, see FIG. 1b.

In case of IV administration (including IV injection and IV dripping using a catheter), drug-loaded MENPs and MENPs alone can also be further navigated to the tumor cells via application of magnetic field gradients. In one embodiment, MENPs that are sufficiently small (e.g., <100 nm) and have an elongated shape (e.g., elliptical, or nano-rods) are used in IV administration. We note that nano-rods propagate in the circulatory system easier than equivalent sized spheres. Such IV-administered MENPs can potentially reach every cell in the body through the body's circulatory system even without application of an external magnetic field. However, in one embodiment, an external magnetic gradient field is applied to guide the MENPs towards the cancer site to further improve the targeting capability. The external magnetic gradient field can be a static field or a dynamic field. One embodiment applies a magnetic field at a level of strength high enough to trigger the nano-electroporation effect to "drive" MENPs, with or without loaded drugs, inside the cancer cells but not high enough to affect the normal cells. This magnetic field can be applied either locally in the vicinity of the tumor or globally to the entire body. The duration of the field application ranges from hours to many days, maintained during the length of IV dripping or for a period of time after the IV injection or IV dripping, depending on the stage and type of cancer. In addition, to further improve the active targeting capability, the MENPs with or without loaded drugs, can be further conjugated with ligands or antibodies that are specific to certain surface receptors or other biomarkers which are over-expressed around the cancer cells. This causes the MENPs in the circulation to attach to cancer cells and facilitates the nano-electroporation by the externally applied magnetic field. In other words, the roles of ligands/antibodies and MENPs are complementary to each other: the ligands/antibodies enable delivery of MENPs towards the surface of cancer cells while MENPs induce the nano-electroporation to move inside cancer cells targeted by the ligands or antibodies. Both effects are specific to cancer cells and therefore the specificity of the combined effect can be significantly improved.

In another embodiment, a rotating or pulsating magnetic field is applied which generates a rotating or pulsating electric polarization on the MENPs to facilitate targeted nano-electroporation. The strength and/or frequency of the rotating or pulsating electric polarization is selected to induce selective nano-electroporation of targeted diseased cells, i.e., the strength and/or frequency rotating or pulsating of the external magnetic field is chosen such that the MENPs only or mainly penetrate the membranes of one or more types of targeted cells and do not or mostly do not penetrate the membranes of other cells. Targeted penetration of the membrane of certain types of diseased cells are better achieved using rotating or pulsating polarization of the MENPs.

In one embodiment, after MENPs have penetrated through the cancer or other diseased cell membranes through nano-electroporation, one or more of the following mechanisms is applied to kill the cancer or diseased cells, (A). Apply an external magnetic field to generate strong enough electric field on the MENPs inside the cancer or diseased cells to kill them, e.g., local electric fields on the order of 1000 V/cm, which can be attained a few nanometers away from MENPs via the application of an external magnetic field on the order of 100 Oe;

(B). Apply an alternating external magnetic field to induce an alternating electric field on the MENPs inside the cancer or diseased cells wherein the strength and frequency of the field is selected such that it disrupts the functions of these cells, thus causes them to die off;

(C). Apply an alternating external magnetic field to generate heat on the MENPs inside the cancer or diseased cells to kill them wherein the strength and frequency of the field is selected to generate sufficient heat to kill the cancer or diseased cells without harming surrounding cells or tissues;

(D). Apply an alternating external magnetic field to induce mechanical motions of the MENPs inside the cancer or diseased cells to disrupt the cell functions or to physically damage the cells from inside, causing them to die off; where the mechanical motions may include linear motion, slicing, collisions or vibrations, or combinations thereof.

In another embodiment, a ferromagnetic resonance strongly dependent on the interaction of MENPs with its nano-environment (in the proximity of a few nanometers away from the nano-particles) is used to selectively disrupt or shut down the operation of certain cellular organneles, e.g. nucleus, microtubules, and others, when MENPs are already inside the cancer cells. The ferromagnetic resonance of MENPs depends on the saturation magnetization, which in turn, because of the ME effect, strongly depends on the electric fields that are associated with the interaction of MENPs with the nano-environment. As the nano-environment changes, so does the saturation magnetization and consequently the ferromagnetic resonance frequency(ies). This resonant frequency or set of resonant frequencies can be varied in a wide range by varying intrinsic properties, e.g. the magneto-crystalline anisotropy energy and the exchange coupling constant, or extrinsic properties, e.g. the shape-induced anisotropy energy. In addition, the resonant frequency(ies) can be controlled by application of an external DC magnetic field. By specifically selecting the resonant frequencies, certain functions of cancer cells can be shut down with a relatively high specificity on demand. For example, the microtubules responsible for cancer cell proliferation could be remotely controlled via ferromagnetic resonance of the MENPs. Namely, the resonant frequency of MENPs in the proximity (of 2 nm) of the microtubules changes because of the changes in the saturation magnetization. The saturation magnetization change is due to the ME effect caused by the interaction of the MENPs and the microtubules. An external AC magnetic field at the new modified resonant frequency can then be applied to disrupt or cause damages to, the microtubules.

Figure 2:
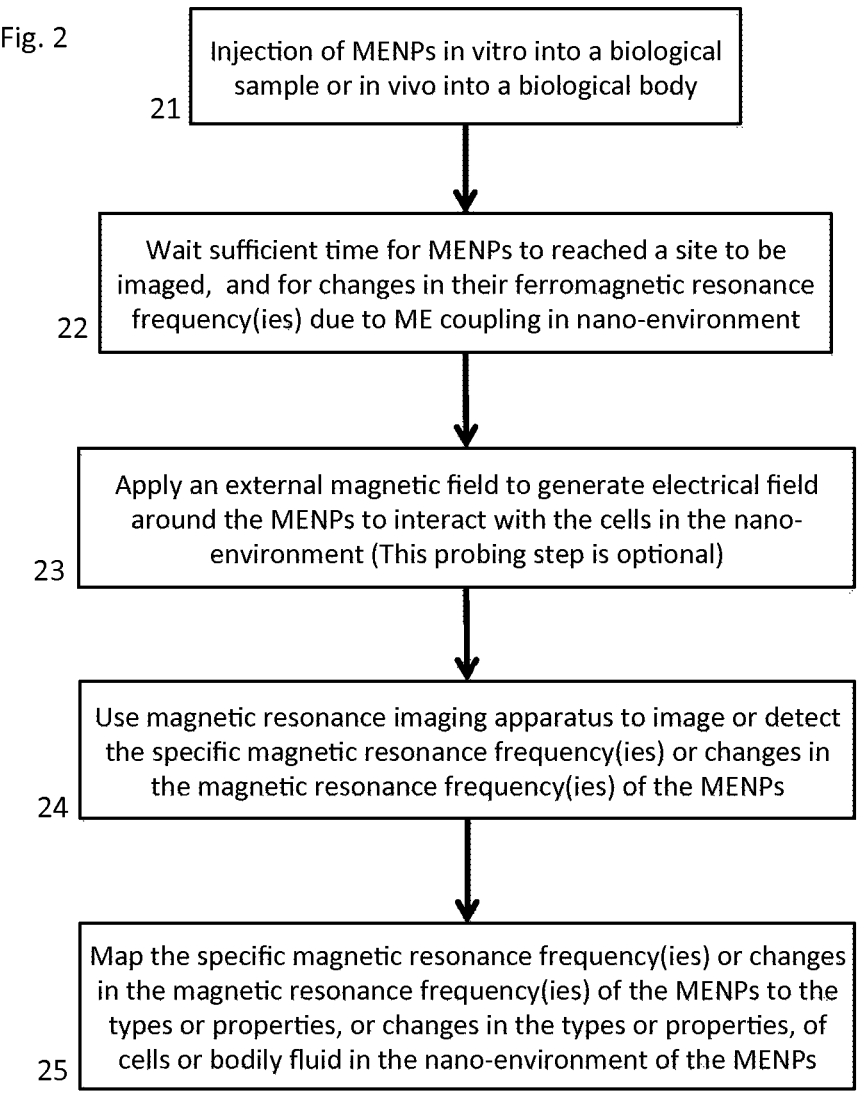
FIG. 2 is a flow chart of an embodiment of functional or diagnostic imaging method or apparatus that detects changes at the cellular level using the ME coupling of MENPs with the nano-environment.

Another embodiment is a functional or diagnostic imaging method or apparatus that detects changes at the cellular level, shown in FIG. 2. The first step 21 in FIG. 2 is the injection of MENPs in vitro into a biological sample or in vivo into a biological system, e.g., an animal or human body. In 22 in FIG. 2, after MENPs have reached a site to be imaged, because of the tight ME coupling of the MENPs, the ionic or electrical properties of different cells or bodily fluid in the immediate nano-environment of the MENPs, or in the cells to which MENPs are bound, cause different changes in the magnetic properties of the MENPs, thus their ferromagnetic resonance frequency(ies). In 24 in FIG. 2, a magnetic resonance imaging apparatus is used to image or detect the specific magnetic resonance frequency(ies) of the MENPs or changes in the magnetic resonance frequency(ies) of the MENPs. In 25 in FIG. 2, the detected or imaged specific magnetic resonance frequency(ies) of the MENPs or changes in the magnetic resonance frequency(ies) of the MENPs are then mapped to the corresponding types or properties, or changes in the types or properties, of cells or bodily fluid in the immediate nano-environment of the MENPs that caused the specific magnetic resonance frequency(ies) or changes in the magnetic resonance frequency(ies) of the MENPs. In 23 in FIG. 2, the embodiment may further include a probing step that first applies an external magnetic field to generate electrical field around the MENPs to interact with the cells in the immediate nano-environment of the MENPs to detect or amplify the effect of ionic or electrical properties of different cells or changes in the properties of cells, e.g., causing nano-electroporation into cancer cells. The interactions of the MENPs with some cells will be further distinguished from other cells. Thereafter, a magnetic resonance imaging apparatus is used to image or detect the effect of the probing due to the further distinguished interactions of the MENPs with different cells, e.g., cancer cells and normal cells.

Figure 3:
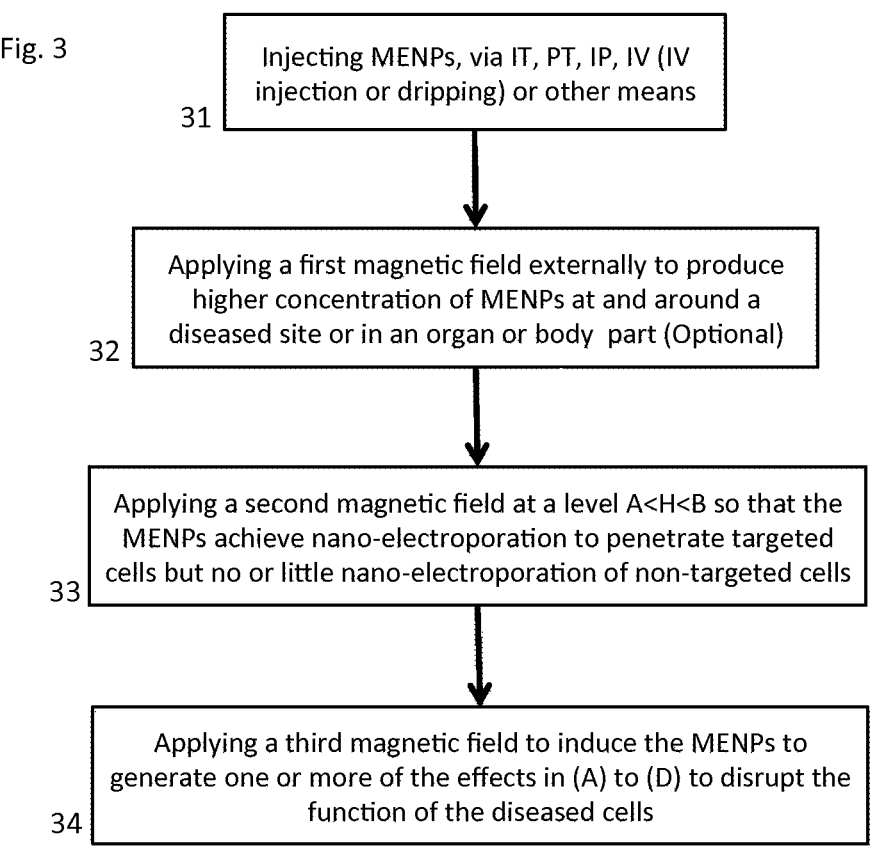
FIG. 3 is a flow chart of an embodiment for targeted killing of cancer or diseased cells using nano-electroporated MENPs that provide a new cancer treatment that is non-toxic or low-toxic.

The above mechanisms of targeted killing of cancer or diseased cells using nano-electroporated MENPs provide a new cancer treatment that is non-toxic or low-toxic. The steps of a preferred embodiment, as shown in FIG. 3, comprise:

Step 1 (31 in FIG. 3): Injecting MENPs, via IT, PT, IP, IV (IV injection or dripping using a catheter) or by other means.

Step 2 (32 in FIG. 3, optional): Applying a first magnetic field externally to produce higher concentration of MENPs at and around a diseased site or in an organ or body part. This step is optional and applicable to a disease site this is localized, e.g., the site of a tumor, and is skipped and not or less applicable when the cancer or diseased cells are widely distributed, e.g., in the circulatory system or metastasized to many sites).

Step 3 (33 in FIG. 3): Applying a second magnetic field at a level A<H<B where A and B are thresholds so that the MENPs achieve nano-electroporation to penetrate targeted cancer or diseased cells but no or little nano-electroporation of healthy or non-targeted cells.

Step 4 (34 in FIG. 3): Applying a third magnetic field to induce the MENPs to generate one or more of the effects in (A) to (D) listed above to disrupt the function of the diseased cells Steps 3 and 4 may be combined into a single step. For a disease that is localized, a localized second and/or third magnetic field this is confined to the disease site is applied. For a disease in which the targeted cells are widely distributed, a wide-area second and/or third magnetic field that covers a large body area or the whole or most part of the body is applied so that cancer or other diseased cells that are circulating in or have metastasized to other parts of the body can be penetrated and killed.

In one embodiment, the strength and/or frequency of the third magnetic field in Step 4 is chosen to cause the MENPs that have penetrated into cancer or diseased cells to kill these targeted cells but does not cause other MENPs that still remain in the body to penetrate or harm healthy or untargeted cells. In another embodiment, a sufficiently long waiting period is inserted between Steps 3 and 4 to give the body sufficient time to excrete most or all of the free MENPs that did not penetrate or bind to cancer or diseased cells out of the body. This reduces the risk of MENPs killing healthy or untargeted cells and gives more freedom in selecting the strength and/or frequency of the third magnetic field in Step 4 to kill the diseased or cancer cells.

Because of the physical (not chemical) nature and the targeting specificity of remote-field-controlled nano-electroporation, the above embodiments can be applied to the multi-drug-resistant (MDR) cancer cell lines that are known to develop immunity to the conventional chemistry-based drugs. For the same reason, the above embodiments can be applied to eradicate isolated (i.e., not aggregated into tumors) cancer stem cells, which are difficult to eradicate using the existing chemistry-based approaches.

Shape, size, ME coupling and other properties are important for the embodiments of this invention. One embodiment for making MENPs with a wide range of properties comprises first depositing a thin film with the required properties via sputter deposition, evaporation, or another deposition technique, and then using ion beam proximity lithography (IBL) or imprint or another advanced lithography to "cut" the thin films into MENPs of desired shapes and sizes.

Figure 4:
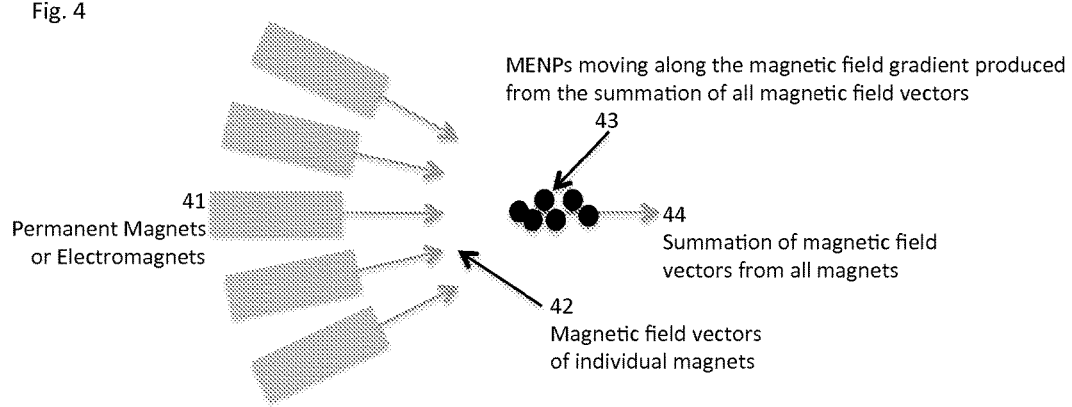
FIG. 4 illustrates the constructive superimposition of magnetic field vectors from multiple magnets at targeted locations inside a patient's body that is sufficient to move MENPs along the superimposed magnetic field gradient or to cause nano-electroporation or killing at the focus point but not elsewhere.

One embodiment is an apparatus that is capable of generating one or more of the first, second and third magnetic fields described above. This embodiment may further include a sensor or imaging device that measures one or more of the following: the strength and/or gradient of the magnetic field at one or more location, the position and/or motion of the MENPs inside the body, or effective local electric field calculated from magnetic imaging of MENPs; and provide the measurements to a feedback control loop which controls the generation and application of the magnetic field to achieve desired strength, frequency and/or distribution of the magnetic field. Yet another embodiment is an apparatus comprising multiple magnets 41 arranged in an enclosure to generate a 3-dimensional magnetic field with sufficient strength in tissues or organ deep inside a human body. The apparatus works by constructively superimposing magnetic field vectors 42 from multiple magnets 41 at targeted locations inside a patient's body, as illustrated in FIG. 4. This allows magnetic field strength sufficiently strong to attract MENPs or MNPs 43, cause them to move along the magnetic field gradient produced from the summation 44 of magnetic field vectors from all the magnets, to cause selective nano-electroporation of cancer cell, and/or to generate one or more of the cancer cell killing mechanisms in (A) to (D), at the targeted location but not strong enough at other locations to cause undesired effects on MENPs that may be still present at other parts of the body. The magnets can be permanent magnets and/or electromagnets. In the case of permanent magnets, they can be physically moved to produce changing magnetic field gradients to guide MENPs to a location inside a human body. In the case of electromagnets, they can be electrically controlled, by selectively turning on or off, up or down, or changing the frequencies of the electric currents driving the electromagnets. The apparatus may further include a Magnetic Resonance Imaging (MRI) or a Magnetic Nano-particle Imaging (MNI) device that produces measurements or images of the 3D distribution of the magnetic field in real time or near real time, and use the measurements to control the generation of the 3D magnetic field to guide MENPs to the desired location inside a human body and/or to generate magnetic field at a desired location to produce nano-electroporation of diseased or cancer cells and/or elicit one or more of the mechanisms in (A) to (D) to kill the diseased or cancer cells. In one embodiment, the MENPs are made with adequately high magnetization value (above 10 emu/cc) to facilitate MNI.

A calibration procedure is performed first when it is applied to a patient at a fixed position to achieve sufficiently accurate mapping of the measurements or images of the 3D distribution of magnetic field to actual locations inside the patient's body. In one embodiment, the calibration procedure establishes a common coordinate system and all measurement points and points inside a human body are mapped into points in this common coordinate system. With accurate MRI or MNI and calibration, this apparatus can achieve "pinpoint" accuracy in killing diseased or cancer cells in the desired location inside a patient's body.

Figure 5:
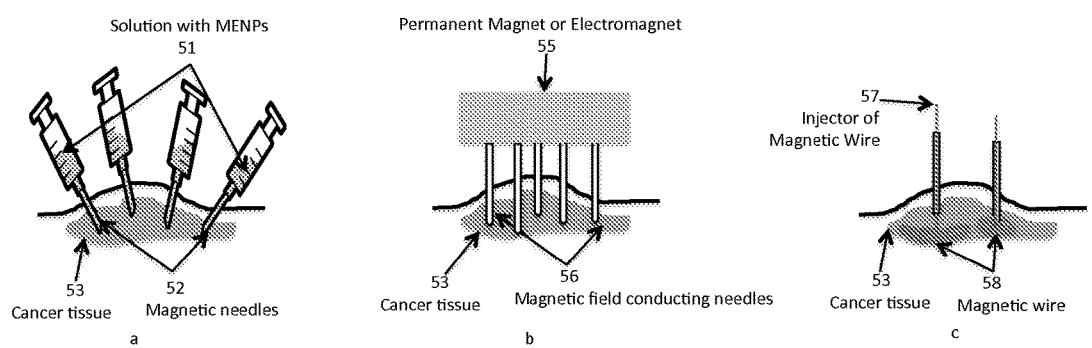
FIG. 5 shows embodiment of (a) magnetic needles, (b) magnetic field conducting needles and (c) magnetic wires for applying magnetic field deep inside tissues with high accuracy.

Another embodiment for "pinpoint" accuracy uses one or more magnetic needles 52 that is used to both inject solutions with MENPs 51 and produce the magnetic field to keep the MENPs in the injected cancer tissue area 53 and for nano-electroporation and cancer cell killing mechanisms, as shown in FIG. 5a. Another embodiment uses one or more highly magnetic field conducting needles 56 to conduct external magnetic field to a location deep inside a patient's body 53, as shown in FIG. 5b. In both cases, multiple needles can be used to generate a magnetic field to cover the volume of the targeted tumor 53. Yet, another embodiment injects or pushes one or more very thin magnetic wires 58 through the hollow of the injection needle of an injecting device 57 into the targeted site 53 to produce sufficient magnetic field at the targeted site for nano-electroporation and cancer cell killing mechanisms. One end of the magnetic wire is kept at the end of the injecting device 57 that is outside the body or connected to handle and the wire can be removed by pulling the wire through the injecting needle when the treatment is completed, as shown in FIG. 5c. The magnetic wire may further be self-coiling such that when it is pushed out of the needle and into the body, it will coil so that the mass of the wire will stay near the site of the injection, as shown in FIG. 5c. Furthermore, the wire may have a dull and smooth or spherical tip so that when it is injected, it causes minimal or no puncture of blood vessels. In all three embodiments illustrated in FIG. 5, multiple needles or magnetic wires can be inserted into different depth and locations in a targeted volume.

Another embodiment uses one or more of the various "pinpoint" embodiments described above, including projection of magnetic field into a site inside the body, using needles or wires, as an initiation to amalgamate MENPs to a site targeted by the "pinpoint." The "pinpoint" method attracts MENPs nearby to the site and/or causes nano-electroporation of MENPs into cancer cells at the site. These MENPs are no longer mobile and further attract other passing by MENPs to the site, forming a positive-feedback self amalgamation process. A "pinpoint" method is used to plant a "seed" for the self amalgamation process that attracts more and more MENPs to the targeted site. The self amalgamation process can also start without applying a "pinpoint" method at sites where nano-electroporation of cancer cells occurs under a broad magnetic field. Once nano-electroporation of cancer cell occurs, the MENPs that entered into the cancer cells can no longer move away and their presence at the site automatically attract other MENPs nearby or passing by, starting a self amalgamation process.

Although the foregoing descriptions of the preferred embodiments of the present inventions have shown, described, or illustrated the fundamental novel features or principles of the inventions, it is understood that various omissions, substitutions, and changes in the form of the detail of the methods, elements or apparatuses as illustrated, as well as the uses thereof, may be made by those skilled in the art without departing from the spirit of the present inventions. Hence, the scope of the present inventions should not be limited to the foregoing descriptions. Rather, the principles of the inventions may be applied to a wide range of methods, systems, and apparatuses, to achieve the advantages described herein and to achieve other advantages or to satisfy other objectives as well.

REFERENCES

1. Armstrong, D. K. et al. (2006). Intraperitoneal cisplatin and paclitaxel in ovarian cancer. New England Journal of Medicine 354, 34.
2. Binggeli, R., Cameron, I. L. (1980). Cellular potentials of normal and cancerous fibroblasts and hepatocytes. Cancer research 40, 1830.
3. Cahill, K. (2010). Molecular electroporation and the transduction of oligoarginines. Physical Biology 7, 016001.
4. Guduru, R., Liang, P., Runowicz, C., Nair, M., Alturi, V., and Khizroev, S. (2013). Magneto-electric MENPs to enable field-controlled high-specificity drug delivery to eradicate ovarian cancer. Scientific Reports 3, 2953.
5. Hong, J. et al. (2012). Room-temperature Magnetic Ordering in Functionalized Graphene. Scientific reports 2, 624.
6. Nair, M., Guduru, R., Liang, P., Hong, J., Sagar, V., and Khizroev, S. (2013). Externally controlled on-demand release of anti-HIV drug using magneto-electric MENPs as carriers. Nature communications 4, 1707.
7. Vasir, J. K., Labhasetwar, V. (2005). Targeted drug delivery in cancer therapy. Technology in cancer research & treatment 4, 363.
8. Yoshida M., et al. (2012). Targeting Anticancer Drug Delivery to Pancreatic Cancer Cells Using a Fucose-Bound MENP Approach. PloS one 7, e39545.
9. Yue, K., Guduru, R., Hong, J., Liang, P., Nair, M., and Khizroev, S. (2012). Magneto-electric MENPs for non-invasive brain stimulation. PloS one 7, e44040.

What are claimed are:

1. A method for achieving high-specificity killing of targeted cells comprising
   administering manufactured Magneto-Electric Nano-Particles (MENPs) that are not loaded with a drug intended for killing targeted cells into a patient's body, wherein the MENPs generate an electric field when subjected to a magnetic field due to magnetic-electric coupling from correlated magnetostrictive and piezoelectric effects of their nanostructures and have a higher tendency to accumulate near or attach to targeted cells through one or more physical forces; and
   after an amount of MENPs have come into sufficient proximity of, attached to or penetrated through the targeted cells' membrane, applying a magnetic field to the MENPs to generate an electric field via the MENPs which is sufficient to cause death of the targeted cells.

2. The method of claim 1 wherein the magnetic field being applied is an alternating field to cause an alternating electric field to disrupt the functions of the targeted cells.

3. The method of claim 1 wherein the strength of the said electric field is controlled by the magnetic field to cause no harm or minimal harm to cells not targeted by the MENPs.

4. The method of claim 1 further comprising using MENPs that have a non-zero magnetic moment and, after the MENPs are administrated into a patient's body, applying an adequately high magnetic field gradients to remotely navigate the MENPs through the blood circulation and/or lymph systems towards a targeted site and/or away from one or more organs or areas to be avoided.

5. The method of claim 1 wherein when the MENPs are administered by injection locally to or near a targeted site, further comprising applying an external magnet field while the MENPs are being injected to attract the MENPs at the targeted site and to cause the MENPs to penetrate the membrane of cancer cells.

6. The method of claim 5 further comprising maintaining an external magnet field for a period of time after the injection.

7. The method of claim 1 further comprising applying a permanent magnetic disk or an electromagnet with desired shape, magnetic field strength and a hole in the middle to a targeted site and administering by injecting to the targeted site using a needle that goes through the hole.

8. The method of claim 1 wherein the MENPs have the shape of nano-rods.

9. The method of claim 4 further comprising applying an external magnetic gradient field to guide the MENPs towards the targeted site, wherein the external magnetic gradient field is a static field and/or a dynamic field.

10. The method of claim 1 wherein the magnetic field is applied locally in the vicinity of a targeted site and/or globally to the entire body.

11. The method of claim 1 wherein applying a magnetic field further comprising applying a first magnetic field locally to a targeted site and applying a second magnetic field globally to the entire body, wherein the two magnetic field is applied concurrently or sequentially.

12. The method of claim 1 further comprising coating or conjugating the MENPs with ligands or antibodies that bind to certain receptors or other biomarkers that are specific to or over-expressed in targeted cells.

13. The method of claim 1 wherein applying a magnetic field further comprising applying a rotating or pulsating magnetic field to generate a rotating or pulsating electric polarization on the MENPs to facilitate targeted nano-electroporation, wherein the strength and/or frequency of the rotating or pulsating electric polarization is selected to induce selective nano-electroporation of targeted cells.

14. The method of claim 1 wherein applying a magnetic field further comprising applying an alternating magnetic field to excite one or more ferromagnetic resonance frequencies of the MENPs to disrupt, kill or cause damages to the mechanisms of the targeted cells.

15. The method of claim 14 further comprising giving the MENPs specific ferromagnetic resonance frequency(ies) by changing their intrinsic and/or or extrinsic properties.

16. The method of claim 14 further comprising applying another magnetic field to control the ferromagnetic resonance frequency(ies) of the MENPs.

* * * * *